United States Patent
Klier et al.

(10) Patent No.: US 6,759,550 B1
(45) Date of Patent: Jul. 6, 2004

(54) OXIDATION OF ALKYL AROMATIC COMPOUNDS TO AROMATIC ACIDS IN AN AQUEOUS MEDIUM

(75) Inventors: John Klier, Midland, MI (US); Christopher J. Tucker, Bay City, MI (US); Thomas H. Kalantar, Midland, MI (US); Kenneth A. Burdett, Midland, MI (US); Daniel Patrick Green, Midland, MI (US); Luciano Piras, Milan (IT); Sergio Schena, Mantova (IT); Guo-shuh John Lee, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 10/149,554

(22) PCT Filed: Nov. 30, 2000

(86) PCT No.: PCT/US00/32582

§ 371 (c)(1),
(2), (4) Date: Nov. 13, 2002

(87) PCT Pub. No.: WO01/53245

PCT Pub. Date: Jul. 26, 2001

Related U.S. Application Data

(60) Provisional application No. 60/176,686, filed on Jan. 18, 2000.

(51) Int. Cl.$^7$ .................. C07C 51/16; C07C 51/255; C07C 45/00; C07C 45/90
(52) U.S. Cl. .................. 562/412; 562/416; 562/417; 568/431
(58) Field of Search .................. 562/412, 416, 562/417; 568/431

(56) References Cited

U.S. PATENT DOCUMENTS

| | | | |
|---|---|---|---|
| 3,907,881 A | 9/1975 | Kuhlmann | 260/524 |
| 4,258,209 A | 3/1981 | Hanotier | 562/412 |
| 4,278,810 A | 7/1981 | Hanotier | 562/412 |
| 4,323,699 A | 4/1982 | Norval | 562/416 |
| 4,357,475 A | 11/1982 | Hanotier et al. | 562/414 |
| 4,892,970 A | 1/1990 | Nowicki et al. | 22/413 |
| 5,112,992 A | 5/1992 | Belmonte et al. | 549/245 |
| 5,359,133 A | 10/1994 | Nazimok et al. | 562/413 |

FOREIGN PATENT DOCUMENTS

| | | |
|---|---|---|
| DE | 2 745 918 | 4/1978 |
| EP | 0 375 812 A1 * | 7/1990 |
| WO | WO 98/29378 | 7/1998 |
| WO | WO 99/18059 | 4/1999 |

OTHER PUBLICATIONS

Catalysis Today, 23, 1995, 69–158; Methodology and scope of metal/bromide autoxidation of hydrocarbons. W. Partenheimer.

Kirk–Othmer Encyclopedia of Chemical Technology, 4$^{th}$ Ed, vol. 18, p. 1006.

React. Kinet. Catal. Lett. vol. 27, No. 2, 1985, pp. 231–233: XP–002033453; M Hronec et al.: "The use of Phase–Transfer Catalysis for the Initiation of P–Xylene Oxidation".

Candian Journal of Chemistry, vol. 67, No. 9, 1989, pp. 1381–1383, XP–000983601; Branko Jursic, "Surfactant assisted permanganate oxidation of aromatic compounds".

* cited by examiner

Primary Examiner—Richard L. Raymond
Assistant Examiner—Zachary Tucker

(57) ABSTRACT

The present invention pertains to an improved method of oxidizing substituted aromatic compounds (such as p xylene) to their corresponding aromatic acids (such as terephthalic acid). The improvement involves carrying out the oxidation reaction in an aqueous medium, wherein the aqueous medium contains at least 30 percent water, preferably up to 30 percent surfactant and preferably a low molecular weight material containing a hydrophilic end group as a co-surfactant. The reaction is carried out at a pH of less than 3.0.

37 Claims, No Drawings

OXIDATION OF ALKYL AROMATIC COMPOUNDS TO AROMATIC ACIDS IN AN AQUEOUS MEDIUM

This case was filed under 35 U.S.C. 371, and is the U.S. National Stage of PCT/US00/32582, filed Nov. 30, 2000. This application claims the benefit of Provisional application No. 60/176,686, filed Jan. 18, 2000.

This invention relates to an improved method for carrying out an oxidation reaction of an alkyl substituted aromatic compound to its corresponding aromatic acid. In particular the invention pertains to carrying out the oxidation reaction in an aqueous medium under pH control, wherein the aqueous medium preferably contains surfactant and preferably a low molecular weight material containing a polar end group as a co-surfactant.

The oxidation reactions of alkyl substituted aromatic compounds to their aromatic acid counterparts are well-known and industrially important reactions. These reactions typically involve contacting the alkyl substituted aromatic precursor with oxygen or an oxygen containing gas, in the presence of a catalyst or catalyst system, typically Mn (II), Co (II), and Br. These reactions have historically been carried out in a solvent composed primarily of organic acids, such as acetic acid or benzoic acid. It would be desirable to use a less expensive, less flammable, less aggressive and more environmentally benign solvent, such as water.

Many aromatic acid precursors are not soluble to any great extent in water, however, leading to difficulties in dispersing the organic phase in the aqueous medium. Poor dispersal of the starting material leads to problems such as reduced yields and reaction rates, and increased byproduct formation, compared to the same reaction run in the more traditional solvent.

Earlier attempts at substituting water for the organic acid solvents typically used in such reactions, including U.S. Pat. Nos. 4,258,209 and 4,218,810 which employ at least five percent by weight together with an organic acid as the solvent. These patents do not use bromine and teach that more catalyst is needed with greater amounts of water. Acid yields reported were relatively low, and expensive processing of the acid product is required. U.S. Pat. No. 4,323,699 employs an aqueous medium and an iodine promoter. Low yields and large amounts of by-product are again reported.

U.S. Pat. No. 4,892,970 teaches a staged process for the oxidation of substituted benzenes, wherein the bromine concentration is increased in the second stage. The second stage of the process is used to increase the yield and reduce the amount of by products otherwise seen in oxidation reactions carried out in an aqueous medium.

Having recognized that the problems with yield and by-product formation were a result of aromatic precursors not being soluble to any great extent in water, the present inventors sought to improve the dispersability of the hydrophobic starting materials. It was discovered that the oxidation reaction does not proceed well if not carried out at a relatively low pH. It was also discovered that surfactants, such as amphiphilic organic compounds like stearic acid or an α-olefin sulfonate or sulfonate salt, could be advantageously used to improve the dispersability of the hydrophobic starting materials. It is believed that the surfactants enhance the dispersion of an aromatic precursor in the aqueous liquid medium. Further, it was discovered that a co-surfactant comprising a low molecular weight polar organic material (such as 1-butanol, toluic acid or benzoic acid) in combination with the surfactant, can contribute greatly to the efficiency of the surfactant in this dispersion process.

Accordingly, the present invention relates to a method for oxidizing substituted aromatic compounds to their corresponding aromatic acids, comprising dispersing the substituted aromatic compound in a liquid medium, contacting the substituted aromatic compound with oxygen or an oxygen-containing gas in the presence of a catalyst, wherein the liquid medium comprises at least 30 per cent by weight (based on the total amount of the feed reaction mixture) water and optionally up to 30 per cent by weight surfactant, and wherein the reaction mixture is at a pH lower than 3.0.

The general reaction materials and conditions which are suitable for this invention (other than the liquid medium) are any of those known in the art {see, for example. Kirk-Othmer Encyclopedia of Chemical Technology, $4^{th}$ Ed, Vol. 18, p. 1006). Accordingly, the starting material can be any substituted aromatic compound having at least one substituent group which is capable of being oxidized to a carboxylic acid or derivative. This includes alkyl, hydroalkyl, aldehyde, hydroxyalkyl, and carboalkyl groups. Of particular importance are the di-alkyl-substituted benzene derivatives, such as meta and para-xylene, and dimethyl naphthalene.

Similarly, the catalyst system can be any of those known in the art for use in oxidation reactions of substituted aromatic compounds. See, for example W. Partenheimer, Catalysis Today, 23 (1995); U.S. Pat. No. 5,359,133; U.S. Pat. No. 5,112,992; and WO 98/29378. Preferred catalysts include manganese (II) and at least one additional metal selected from the group consisting of cobalt, nickel, chromium, zirconium, hafnium, cerium, palladium, and mixtures thereof. It is preferred that the second metal be selected from the group consisting of cerium, cobalt, hafnium and zirconium. A bromine-affording material (which may be elemental bromine, a bromide or bromate salt, hydrobromic acid, a bromine substituted organic compound, or a mixture thereof is also advantageously added, as is known in the art. The catalyst can be added to the liquid before, after or together with the to substituted aromatic compound. The amount of catalyst components used is within the ranges known in the art. For the purposes of the present invention the bromine concentration (as bromine element or ion) in the total feed reaction mixture is in the range of 100 to 10000 ppm w/w, preferably in the range of 500 to 6000, most preferably in the range of 1000 to 4000. The ratio bromine to metals is in the range of from 0.8 to 6, preferably in the range of 1 to 4, most preferably in the range of 1.5 to 3. The ratio Mn to additional metal is in the range of 0.5 to 4, preferably in the range of 1 to 3.

The oxygen-containing gas supplied to the reactor can be pure oxygen, air, oxygen-enriched air or a mixture of oxygen with an inert gas, and can be added to the reactor by any method known in the art.

The liquid medium comprises at least 30 percent by weight water. It has been discovered that the oxidation reaction, when conducted using as reaction medium only water, does not proceed well (low yield, low rate and low product purity) when the pH of the reaction medium is higher than 3.0. Therefore, the pH of the reaction mixture should be less than 3.0 preferably less than 2.5, most preferably less than 2.0. It is preferred that an acid such as acetic acid, methanesulfonic acid, or sulfuric acid, or others, be added to the aqueous medium in an amount sufficient to bring the pH of the reaction mixture to the desired level. It is preferred that an amount of surfactant, up to 30 per cent by weight based on the total feed reaction mixture, also be added to the reaction mixture. A low molecular weight molecule containing a hydrophilic end group, or "co-surfactant" should also be present to increase the efficiency of the surfactant. It is preferred that the co-surfactant have a molecular weight less than 1000. The co-surfactant can advantageously be a by product or intermediate in the oxidation reaction of the substituted aromatic compound. For example, in the oxidation of xylenes to the corresponding phthalic acids, preferred co-surfactants include benzoic, toluic and acetic acid. The co-surfactant is preferably present in a concentration of from 0.1 to 10 percent by weight based on the total amount of the feed reaction mixture including any co-surfactant which may be generated in the oxidation reaction. It should be noted that the co-surfactant is preferably an acid, and this helps to bring the pH to the preferred levels.

The water content is preferably in the range of from 30 to 95 percent, most preferably in the range of from 50 to 85 percent. The surfactant concentration, including any co-surfactant used, depends on the surfactant specifically selected: any suitable amount, up to a concentration of 30% on a weight basis can be used for the purpose of the present invention. The surfactant is any amphiphilic organic liquid or solid compound, miscible with water in the specific conditions and range of concentration suitable for the application, with preferred surfactants including stearic acid, benzenesulfonic acid and α-olefin sulfonates (such as Witconate AOS-2024™), or sodium lauryl sulfate. The surfactant may be added initially to the aqueous phase before introducing the organic phase, or may be introduced with the organic phase, or both in combination. The surfactant should be added in an amount sufficient to form a dispersion, emulsion, miniemulsion, or a microemulsion of the substituted aromatic compound in the aqueous liquid medium, where microemulsion is a dispersion characterized by very small droplets size and clear homogeneous appearance. Generally, it is preferred if the surfactant is present in an amount of from 0.05 to 10 percent by weight based on the total amount of the feed reaction mixture.

The reaction is then run under conditions based on these practiced in the industrial oxidation for para-xylene. It may be run in batch, semi-batch, or continuous modes. It is preferred that the temperature of the reaction be between 180 to 230° C., more preferably, 200 to 220° C., and most preferably about 215° C. It is also preferred that the pressure of the reaction be in the range of from 10 to 28.5 bar, more preferably in the range of from 15.8 to 23.6 bar, and most preferably about 21.4 bar. The effectiveness of the present invention may be seen in the following Examples:

EXAMPLES

In the following Examples, the liquid medium, substituted aromatic compound, and catalysts were placed in a 1 L Titanium Parr reactor, the headspace of which having been purged with nitrogen. The reactor was stirred at 1200–1600 rpm, and pressurized with nitrogen to 21 bar g. The temperature of the reactor contents was then raised to 215° C. over the course of 1 hour. When the reactor reached 200° C., the following gas flows were established: 736 cc $N_2$/min at STP to headspace and 552 cc air/min at STP sparged into the liquid phase. A horizontal baffle in the reactor, just below the level of the liquid surface was used to prevent the entrainment of headspace gas into the liquid phase. The reaction was allowed to continue for 180 min., after which time the air flew was stopped and the reactor cooled. The solids were isolated, weighed and analyzed by $^1$H NMR. Identical runs were conducted with and without surfactant.

Control (with Acetic Acid)

To demonstrate the current state of the art, two identical control experiments with acetic acid as the liquid medium were conducted and the results averaged. The following materials were charged to the reactor in each experiment: p-xylene 20 g; water 20 g, acetic acid 460 g, $Mn(CH_3CO_2)_2$ $6H_2O$ 0.291 g, $Co(CH_3CO_2)_2$ $6H_2O$ 0.283 g, $MnBr_2$ 0.269 g, for a total weight of 500.8 grams. The reaction was stirred at 1600 rpm, and allowed to continue for 180 minutes. The following average results were obtained: mass solids 12.675 g (38% yield of terephthalic acid based on xylene, 41% conversion of p-xylene; 1H NMR analysis shows: 91.8 mol % terephthalic acid, 4.7 mol % 4-carboxybenzaldehyde, and 3.4 mol % p-toluic acid).

Example 1

The following materials were charged to the reactor: p-xylene 10 g; water 599.7 g, acetic acid 68.5 g, $CoBr_2$ $6H_2O$ 1.24 g, $Co(CH_3CO_2)_2$ $6H_2O$ 0.13 g, $MnBr_2$ 2.93 g, for a total weight of 682.46 g. The pH of the reaction contents was approximately 1.3. The reaction was stirred at 1200 rpm. The following results were obtained: mass solids 7.2 g (38.6% yield of terephthalic acid based on xylene, 45.9% conversion of p-xylene; $^1$H NMR analysis shows: 84 mol % terephthalic acid, 10 mol % 4-carboxybenzaldehyde, and 6 mol % p-toluic acid).

Example 2

The following materials were charged to the reactor: p-xylene 10 g; water 588.3 g, acetic acid 67.1 g, $CoBr_2$ $6H_2O$ 1.24 g, $Co(CH_3CO_2)_2$ $6H_2O$ 0.13 g, HnBr2 2.94 g, for a total weight of 671 g, 1.3 g {active basis) Witconate AOS-2024™ surfactant was then added. The pH of the reaction contents was approximately 1.3. The reaction was stirred at 1600 rpm. The following results were obtained: mass solids 9.2 g {40.5% yield of terephthalic acid based on xylene, 57.8% conversion of p-xylene; $^1$H NMR analysis shows: 70 mol % terephthalic acid, 16 mol % 4-carboxybenzaldehyde, 12 mol % p-toluic acid and 2.5% p-xylene).

Accordingly, the degree of conversion of xylene to oxidation products was greater in the presence of surfactant than in its absence.

Example 3

The following materials were charged to the reactor: p-xylene 10 g; water 640 g, acetic acid 0.0 g, $Co(CH_3CO_2)_2$ $6H_2O$ 1.09 g, $Mn(CH_3CO_2)_2$ $6H_2O$ 3.37 g, 48% aqueous HBr 5.9 g, for a total weight of 678 g. 1.3 g {active basis) Witconate AOS-2024™ surfactant was added. The pH of the reaction mixture was approximately 3. The reaction was stirred at 1600 rpm. The following results were obtained: mass solids 0 g (0% yield of terephthalic acid based on xylene, 0% conversion of p-xylene).

Example 4

The following materials were charged to the reactor: p-xylene 10 g; water 640 g, acetic acid 0.0 g, $Co(CH_3CO_2)_2$ $6H_2O$ 1.08 g, $Mn(CH_3CO_2)_2$ $6H_2O$ 3.37 g, 48% aqueous HBr 6.2 g, methanesulfonic acid 2.0 mL, for a total weight of 678 g. 1.3 g (active basis) Witconate AOS-2024™ surfactant was added. The pH of the reaction mixture was approximately 1.8. The reaction was stirred at 1600 rpm. The following results were obtained: mass solids 5.99 g (37% yield of terephthalic acid based on xylene, 37% conversion of p-xylene; $^1$H NMR analysis shows: 100 mol % terephthalic acid}. Thus, improved results are obtained at a relatively lower pH.

It should be realized by one of ordinary skill in the art that the invention is not limited to the exact configuration or methods illustrated above, but that various modifications may be made without departing from the spirit and scope of the invention as described within the following claims.

What is claimed is:

1. A method for oxidizing alkyl substituted aromatic compounds to their corresponding aromatic acid, comprising:
    a) dispersing the alkyl substituted aromatic compound in a liquid medium including a sufficient amount of a surfactant to form a dispersion or emulsion;
    b) contacting the alkyl substituted aromatic compound with oxygen or an oxygen-containing gas in the presence of a catalyst containing a bromine-affording material; wherein the liquid medium comprises greater than thirty percent by weight water based on the total feed reaction mixture, and wherein the pH of the liquid medium is less than 3.0.
2. The method of claim 1 wherein the alkyl substituted aromatic compound is a xylene.
3. The method of claim 1 wherein the alkyl substituted aromatic compound is a dimethyl naphthalene.
4. The method of claim 1 wherein the pH is less than 2.0.
5. The method of claim 1 wherein the pH is less than 1.5.
6. The method of claim 1 wherein the surfactant is an amphiphilic organic compound.
7. The method of claim 6 wherein the surfactant is stearic acid.
8. The method of claim 6 wherein the surfactant is an alpha olefin sulfonate.
9. The method of claim 6 wherein the surfactant is sodium lauryl sulfate.
10. The method of claim 1 wherein the surfactant is added in an amount of 0.05 to 30 percent by weight based on total feed reaction mixture.
11. The method of claim 1 wherein the surfactant is added in an amount sufficient to form a micro emulsion.
12. The method of claim 1 wherein the liquid medium further comprises a low molecular weight molecule containing a hydrophilic end group as a co-surfactant.
13. The method of claim 12 wherein the co-surfactant is an intermediate or by product in the oxidation reaction of the substituted aromatic compound to its corresponding aromatic acid.
14. The method of claim 12 wherein the co-surfactant is present in an amount of from 0.1 to 10 percent by weight based on the total feed reaction mixture.
15. The method of claim 12 wherein the co-surfactant is selected from the group consisting of benzoic acid, toluic acid and acetic acid.
16. The method of claim 1 wherein the liquid medium comprises 30 to 95 percent by weight of water.
17. The method of claim 16 wherein the liquid medium comprises 50 to 85 percent by weight of water.
18. The method of claim 1 wherein the catalyst comprises Mn (II), a bromine-affording material and at least one additional metal selected from the group consisting of Co (II), Ni, Cr, Zr, Hf, Pd and Ce.
19. The method of claim 18 wherein the bromine-affording material is elemental Bromine.
20. The method of claim 18 wherein the bromine-affording material is a Bromate salt.
21. The method of claim 18 wherein the bromine-affording material is a bromide salt.
22. The method of claim 18 wherein the bromine-affording material is hydrobromic acid.
23. The method of claim 18 wherein the bromine-affording material is bromine-substituted organic compound.
24. The method of claim 18 wherein the bromine concentration in the total feed reaction mixture is in the range of 100 to 10000 ppm.
25. The method of claim 24 wherein the bromine concentration in the total feed reaction mixture is in the range of 500 to 6000 ppm.
26. The method of claim 25 wherein the bromine concentration in the total feed reaction mixture is in the range of 1000 to 4000 ppm.
27. The method of claim 18 wherein the ratio of bromine to metals is in the range of from 0.8 to 6.
28. The method of claim 27 wherein the ratio of bromine to metals is in the range of from 1 to 4.
29. The method of claim 28 wherein the ratio of bromine to metals is in the range of from 1.5 to 3.
30. The method of claim 29 wherein the ratio of Mn to other metals is in the range of 0.5 to 4.
31. The method of claim 30 wherein the ratio of Mn to other metals is in the range of 1 to 3.
32. The method of claim 1 wherein the step of contacting the alkyl substituted aromatic compound with oxygen is conducted at a temperature in the range of from 180 to 230° C.
33. The method of claim 32 wherein the temperature is in the range of from 200 to 220° C.
34. The method of claim 33 wherein the temperature is 215° C.
35. The method of claim 1 wherein the step of contacting the alkyl substituted aromatic compound with oxygen is conducted at a pressure in the range of from 10 to 28.5 bar.
36. The method of claim 35 wherein the pressure is in the range of from 15.8 to 23.6 bar.
37. The method of claim 36 wherein the pressure is 21.4 bar.

* * * * *